US006599732B1

(12) United States Patent
Rayapati et al.

(10) Patent No.: US 6,599,732 B1
(45) Date of Patent: Jul. 29, 2003

(54) REGULATION OF CARBON ASSIMILATION

(75) Inventors: P. John Rayapati, Decatur, IL (US); Corey M. Crafton, Decatur, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 09/606,312

(22) Filed: Jun. 29, 2000

Related U.S. Application Data
(60) Provisional application No. 60/141,001, filed on Jun. 29, 1999.

(51) Int. Cl.$^7$ ............ C12N 9/88; C12N 12/00; C12N 1/20; C07H 21/04

(52) U.S. Cl. ............ 435/252.32; 435/320; 435/252.33; 435/232; 536/23.2

(58) Field of Search .................. 435/232, 252.32, 435/252.33, 320.1; 536/23.2

(56) References Cited

U.S. PATENT DOCUMENTS

| 4,757,009 A | 7/1988 | Sano et al. ............ 435/106 |
| 5,876,983 A | 3/1999 | Sugimoto et al. ......... 435/106 |

FOREIGN PATENT DOCUMENTS

| EP | 0 143 195 A1 | 6/1985 |
| EP | 0 212 649 A3 | 3/1987 |
| EP | 0 212 649 A2 | 3/1987 |
| EP | 0 358 940 A1 | 3/1990 |
| EP | 0 723 011 A1 | 7/1996 |
| EP | 0 754 756 A1 | 1/1997 |
| EP | 0 756 007 A2 | 1/1997 |
| EP | 0 756 007 A3 | 10/1997 |
| EP | 0 857 784 A2 | 8/1998 |
| WO | WO 99/53035 | 10/1999 |

OTHER PUBLICATIONS

Vance, C.P., and Stade, S., "Alfalfa Root Nodule Carbon Dioxide Fixation," *Plant Physiol.* 75:261–264 (1984).

Yoshinaga, T. et al., "Purification and Molecular Properties of Allosteric Phosphoenolpyruvate Carboxylase from *Escherichia coli,*" *J. Biochem.* 68:747–750 (1970).

Dialog file 351, Accession No. 1996–195282, Derwent WPI abstract for JP 80 66189 A.

International Search Report for International Application No. PCT/US99/14437, mailed Jun. 27, 2000.

Sano, K. et al., "Amplification of the Phosphoenol Pyruvate Carboxylase Gene of *Brevibacterium lactofermentum* to Improve Amino Acid Production," *Agric. Biol. Chem.* 51:597–599 (1987).

Ueno, Y. et al., "Regulatory phosphorylation of plant phosphoenolpyruvate carboxylase: role of a conserved basic residue upstream of the phosphorylation site," *FEBS Lett.* 417:57–60 (1997).

Valle, F. et al., "Basic and applied aspects of metabolic diversity: the phosphoenolpyruvate node," *J. Ind. Microbiol.* 17:458–462 (1996).

Pathirana, M.S. et al., "Analysis of phosphoenolpyruvate carboxylase gene structure and expression in alfalfa nodules," *The Plant Journal* 12:293–304 (1997).

Peters–Wendisch, P.G. et al., "Pyruvate carboxylase from *Corynebacterium glutamicum*: characterization, expression and inactivation of the pyc gene," *Microbiolgy* 144:915–927 (Apr. 1998).

Saito, H., and Miura, K.–I., "Preparation of Transforming Deoxyribonucleic Acid by Phenol Treatment," *Biochim. Biophys. Acta* 72: 619–629 (1963).

O'Regan, M. et al., "Cloning and nucleotide sequence of the phosphoenolpyruvate carboxylase–coding gene of *Corynebacterium glutamicum* ATCC13032," *Gene* 77:237–251 (1989).

Ozaki, H., and Shiio, I., "Production of Lysine by Pyruvate Kinase Mutants of *Brevibacterium flavum*," *Agric. Biol. Chem.* 47:1569–1576 (1983).

Pathirana, S.M. et al., "Alfalfa root nodule phosphoenolpyruvate carboxylase: characterization of the cDNA and expression in effective and plant–controlled ineffective nodules," *Plant Mol. Biol.* 20:437–450 (1992).

Mori, M., and Shiio, I., "Multiple Interaction of Fructose 1,6–Bisphosphate and Other Effectors on Phosphoenolpyruvate Carboxylase from *Brevibacterium flavum* and Its Aspartate–producing Mutant," *Argic. Biol. Chem.* 50:2605–2614 (1986).

Morikawa, M. et al., "Phosphoenolpyruvate Carboxylase of E. coli: Discrimination of Regulatory Sites for Four Kinds of Allosteric Effectors by the Method of Genetic Desensitization," *Biochem. Biophys. Res. Commun.* 45:689–694 (1971).

Morikawa, M. et al., "Studies on the Allosteric Properties of Mutationally Altered Phosphoenolpyruvate Carboxylases of *Escherichia coli*: Discrimination of Allosteric Sites," *J. Biochem.* 81:1473–1485 (1977).

(List continued on next page.)

*Primary Examiner*—Rebecca E. Prouty
*Assistant Examiner*—Malgorzata A. Walicka
(74) *Attorney, Agent, or Firm*—Sterne, Kessler, Goldstein & Fox, P.L.L.C.

(57) ABSTRACT

The present invention provides a method of increasing the productivity of a microorganism by improving the assimilation of carbon dioxide. Specifically, the invention provides a polypeptide having phosphoenolpyruvate carboxylase activity which does not require acetyl coenzyme A for activation and is desensitized to feedback inhibition by aspartic acid, and to genes coding for this polypeptide. A gene encoding a PEP carboxylase that is not regulated by acetyl-CoA or aspartic acid can improve carbon flow from the three carbon intermediate PEP to the four carbon intermediate OAA, contribute to compounds derived from OAA, and increase amino acid biosynthesis. The invention further provides recombinant DNA molecules containing these genes, bacteria transformed with these genes, and a method of producing amino acids using the transformed bacteria.

17 Claims, 1 Drawing Sheet

OTHER PUBLICATIONS

Kodaki, T. et al., "Cloning of Phosphoenolpyruvate Carboxylase Gene from a Cyanobacterium, *Anacystis nidulans*, in *Escherichia coli*," *J. Biochem.* 97:533–539 (1985).

Millard, C.S. et al., "Enhanced Production of Succinic Acid by Overexpression of Phosphoenolpyruvate Carboxylase in *Escherichia coli*," *Applied and Environmental Microbiology* 62:1808–1810 (1996).

Mori, M., and Shiio, I., "Synergistic Inhibition of Phosphoenolpyruvate Carboxylase by Aspartate and 2–Oxoglutarate in *Brevibacterium flavum*," *J. Biochem.* 98:1621–1630 (1985).

Jiao, J.–A., and Chollet, R., "Regulatory Seryl–Phophorylation of $C_4$ Phosphoenolpyruvate Carboxylase by a Soluble Protein Kinase from Maize Leaves," *Arch. Biochem. Biophys.* 269:526–535 (1989).

Kameshita, I. et al., "Reversible Desensitization of Phosphoenolpyruvate Carboxylase to Multiple Effectors by Butanedione," *Biochem. Biophys. Res. Commun.* 76:905–909 (1977).

Kameshita, I. et al., "Phosphoenolpyruvate Carboxylase of *Escherichia coli*," *J. Biochem.* 84:795–803 (1978).

Duff, S.M.G. et al., "Kinetic analysis of the non–phosphorylated, in vitro phosphorylated, and phosphorylation–site–mutant (Asp8) forms of intact recombinant $C_4$ phosphoenolpyruvate carboxylase from sorghum," *Eur. J. Biochem.* 228:92–95 (1995).

Eikmanns, B.J. et al., "The phosphoenolpyruvate carboxylase gene of *Corynebacterium glutamicum*: Molecular cloning, nucleotide sequence, and expression," *Mol. Gen. Genet.* 218:330–339 (1989).

Giglioli–Guivarc'h, N. et al., "Flow Cytometric Analysis of Cytosolic pH of Mesophyll Cell Protoplasts From the Crabgrass *Digitaria sanguinalis*," *Cytometry* 23:241–249 (1996).

EMBL entry, Accession No. L39371, from Pathirana, S.M. et al.(1996).

Written Opinion for International Application PCT/US99/14437, mailed on Jul. 19, 2001.

EMBL entry, Accession No. M83086, from Pathirana, S.M. et al. (1992).

SWISS–PROT Entry, Accession No. Q02735, from Pathirana, S.M. et al. (1993).

SEQUENCE LISTING

<160> NUMBER OF SEQ ID NOS: 7

<210> SEQ ID NO 1
<211> LENGTH: 2901
<212> TYPE: DNA
<213> ORGANISM: Medicago sativa
<220> FEATURE:
<221> NAME/KEY: CDS
<222> LOCATION: (1)..(2901)

<400> SEQUENCE: 1

| | | | | | | | | | | | | | | | | |
|---|---|---|---|---|---|---|---|---|---|---|---|---|---|---|---|---|
| atg | gca | aac | aag | atg | gaa | aaa | atg | gca | tca | att | gat | gca | cag | ctt | aga | 48 |
| Met | Ala | Asn | Lys | Met | Glu | Lys | Met | Ala | Ser | Ile | Asp | Ala | Gln | Leu | Arg | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| caa | ttg | gtt | cct | gca | aaa | gtg | agt | gaa | gat | gat | aaa | ctt | att | gag | tat | 96 |
| Gln | Leu | Val | Pro | Ala | Lys | Val | Ser | Glu | Asp | Asp | Lys | Leu | Ile | Glu | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| gat | gct | ttg | ttg | ttg | gat | cgg | ttt | ctt | gat | att | ctt | caa | gat | tta | cat | 144 |
| Asp | Ala | Leu | Leu | Leu | Asp | Arg | Phe | Leu | Asp | Ile | Leu | Gln | Asp | Leu | His | |
| | | 35 | | | | | 40 | | | | | 45 | | | | |

| | | | | | | | | | | | | | | | | |
|---|---|---|---|---|---|---|---|---|---|---|---|---|---|---|---|---|
| gga | gag | gat | ctg | aag | gat | tct | gtt | caa | gaa | gtg | tat | gaa | ctg | tct | gct | 192 |
| Gly | Glu | Asp | Leu | Lys | Asp | Ser | Val | Gln | Glu | Val | Tyr | Glu | Leu | Ser | Ala | |
| | 50 | | | | | 55 | | | | | 60 | | | | | |

| | | | | | | | | | | | | | | | | |
|---|---|---|---|---|---|---|---|---|---|---|---|---|---|---|---|---|
| gaa | tat | gaa | aga | aag | cat | gat | cct | aag | aaa | ctt | gaa | gag | ctt | gga | aat | 240 |
| Glu | Tyr | Glu | Arg | Lys | His | Asp | Pro | Lys | Lys | Leu | Glu | Glu | Leu | Gly | Asn | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttg | atc | aca | agt | ttc | gat | gca | ggt | gac | tca | att | gtt | gtt | gcc | aag | tcc | 288 |
| Leu | Ile | Thr | Ser | Phe | Asp | Ala | Gly | Asp | Ser | Ile | Val | Val | Ala | Lys | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| ttt | tca | cac | atg | ctt | aac | ttg | gcc | aac | tta | gct | gaa | gag | gtt | caa | att | 336 |
| Phe | Ser | His | Met | Leu | Asn | Leu | Ala | Asn | Leu | Ala | Glu | Glu | Val | Gln | Ile | |
| | | | 100 | | | | | 105 | | | | | 110 | | | |

| | | | | | | | | | | | | | | | | |
|---|---|---|---|---|---|---|---|---|---|---|---|---|---|---|---|---|
| gcg | cac | cgc | cga | agg | aac | aag | ttg | aag | aaa | ggt | gat | ttt | agg | gat | gag | 384 |
| Ala | His | Arg | Arg | Arg | Asn | Lys | Leu | Lys | Lys | Gly | Asp | Phe | Arg | Asp | Glu | |
| | | 115 | | | | | 120 | | | | | 125 | | | | |

| | | | | | | | | | | | | | | | | |
|---|---|---|---|---|---|---|---|---|---|---|---|---|---|---|---|---|
| agc | aat | gca | acc | act | gaa | tct | gac | att | gag | gaa | act | ctc | aag | aaa | ctt | 432 |
| Ser | Asn | Ala | Thr | Thr | Glu | Ser | Asp | Ile | Glu | Glu | Thr | Leu | Lys | Lys | Leu | |
| | 130 | | | | | 135 | | | | | 140 | | | | | |

| | | | | | | | | | | | | | | | | |
|---|---|---|---|---|---|---|---|---|---|---|---|---|---|---|---|---|
| gtg | ttt | gac | atg | aag | aaa | tct | cct | caa | gag | gtt | ttt | gat | gca | ttg | aag | 480 |
| Val | Phe | Asp | Met | Lys | Lys | Ser | Pro | Gln | Glu | Val | Phe | Asp | Ala | Leu | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| aac | cag | act | gtt | gat | ctt | gtt | ctt | act | gct | cat | cct | act | cag | tcg | gtt | 528 |
| Asn | Gln | Thr | Val | Asp | Leu | Val | Leu | Thr | Ala | His | Pro | Thr | Gln | Ser | Val | |
| | | | | 165 | | | | | 170 | | | | | 175 | | |

| | | | | | | | | | | | | | | | | |
|---|---|---|---|---|---|---|---|---|---|---|---|---|---|---|---|---|
| cgt | cga | tct | ttg | ctt | caa | aag | cac | gga | agg | gta | agg | aac | tgt | tta | tct | 576 |
| Arg | Arg | Ser | Leu | Leu | Gln | Lys | His | Gly | Arg | Val | Arg | Asn | Cys | Leu | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| caa | ttg | tat | gct | aaa | gac | atc | act | cct | gat | gat | aag | cag | gag | ctt | gat | 624 |
| Gln | Leu | Tyr | Ala | Lys | Asp | Ile | Thr | Pro | Asp | Asp | Lys | Gln | Glu | Leu | Asp | |
| | | 195 | | | | | 200 | | | | | 205 | | | | |

| | | | | | | | | | | | | | | | | |
|---|---|---|---|---|---|---|---|---|---|---|---|---|---|---|---|---|
| gaa | gct | ctc | cag | agg | gag | att | caa | gct | gca | ttc | cgt | act | gac | gaa | atc | 672 |
| Glu | Ala | Leu | Gln | Arg | Glu | Ile | Gln | Ala | Ala | Phe | Arg | Thr | Asp | Glu | Ile | |
| | 210 | | | | | 215 | | | | | 220 | | | | | |

| | | | | | | | | | | | | | | | | |
|---|---|---|---|---|---|---|---|---|---|---|---|---|---|---|---|---|
| aag | agg | act | cca | cca | act | ccc | caa | gat | gaa | atg | aga | gct | ggg | atg | agt | 720 |
| Lys | Arg | Thr | Pro | Pro | Thr | Pro | Gln | Asp | Glu | Met | Arg | Ala | Gly | Met | Ser | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| tac | ttc | cat | gaa | aca | att | tgg | aag | ggt | gtc | cct | aaa | ttt | ctt | cgc | cgt | 768 |
| Tyr | Phe | His | Glu | Thr | Ile | Trp | Lys | Gly | Val | Pro | Lys | Phe | Leu | Arg | Arg | |
| | | | | 245 | | | | | 250 | | | | | 255 | | |

-continued

| | |
|---|---|
| gtt gat acg gca ttg aag aac ata ggg att aac gaa cgt gtt ccc tat<br>Val Asp Thr Ala Leu Lys Asn Ile Gly Ile Asn Glu Arg Val Pro Tyr<br>260 265 270 | 816 |
| aat gct cct ctt att caa ttt tct tct tgg atg ggt ggt gat cgt gac<br>Asn Ala Pro Leu Ile Gln Phe Ser Ser Trp Met Gly Gly Asp Arg Asp<br>275 280 285 | 864 |
| ggt aat cca aga gtg act cct gaa gtg aca agg gat gtt tgc tta cta<br>Gly Asn Pro Arg Val Thr Pro Glu Val Thr Arg Asp Val Cys Leu Leu<br>290 295 300 | 912 |
| gct aga atg atg gct gct aac ttg tat tat tca cag ata gaa gat ctt<br>Ala Arg Met Met Ala Ala Asn Leu Tyr Tyr Ser Gln Ile Glu Asp Leu<br>305 310 315 320 | 960 |
| atg ttt gaa ctt tct atg tgg cgt tgc aat gac gag cta cgt gtt cgc<br>Met Phe Glu Leu Ser Met Trp Arg Cys Asn Asp Glu Leu Arg Val Arg<br>325 330 335 | 1008 |
| gca gaa gaa ctt cac agg aat tcc aag aaa gat gaa gtt gca aaa cac<br>Ala Glu Glu Leu His Arg Asn Ser Lys Lys Asp Glu Val Ala Lys His<br>340 345 350 | 1056 |
| tat ata gag ttt tgg aaa aaa att cct ttg aat gaa cca tac cgt gtt<br>Tyr Ile Glu Phe Trp Lys Lys Ile Pro Leu Asn Glu Pro Tyr Arg Val<br>355 360 365 | 1104 |
| gta ctc ggg gag gta agg gac aag ctc tat cgc act cgt gag cgt tct<br>Val Leu Gly Glu Val Arg Asp Lys Leu Tyr Arg Thr Arg Glu Arg Ser<br>370 375 380 | 1152 |
| cgt tat ctc cta gct cat ggc tac tgt gaa att cct gaa gaa gcc aca<br>Arg Tyr Leu Leu Ala His Gly Tyr Cys Glu Ile Pro Glu Glu Ala Thr<br>385 390 395 400 | 1200 |
| ttc acc aat gtc gat gag ttt ctg gaa cct ctt gaa ctc tgc tac aga<br>Phe Thr Asn Val Asp Glu Phe Leu Glu Pro Leu Glu Leu Cys Tyr Arg<br>405 410 415 | 1248 |
| tca ctc tgt gct tgt ggt gat cgt gca att gct gat gga agc ctt ctt<br>Ser Leu Cys Ala Cys Gly Asp Arg Ala Ile Ala Asp Gly Ser Leu Leu<br>420 425 430 | 1296 |
| gat ttc ttg agg caa gtt tcc act ttt gga ctg tca ctt gta agg ctt<br>Asp Phe Leu Arg Gln Val Ser Thr Phe Gly Leu Ser Leu Val Arg Leu<br>435 440 445 | 1344 |
| gat ata cgg caa gag tct gat cgt cac act gac gtg atg gat gcc att<br>Asp Ile Arg Gln Glu Ser Asp Arg His Thr Asp Val Met Asp Ala Ile<br>450 455 460 | 1392 |
| acc aaa cat ttg gaa att gga tcc tac caa gaa tgg tct gaa gaa aaa<br>Thr Lys His Leu Glu Ile Gly Ser Tyr Gln Glu Trp Ser Glu Glu Lys<br>465 470 475 480 | 1440 |
| aga cag gaa tgg ctt ttg tcc gag ttg att ggc aaa agg cca ctc ttt<br>Arg Gln Glu Trp Leu Leu Ser Glu Leu Ile Gly Lys Arg Pro Leu Phe<br>485 490 495 | 1488 |
| gga cct gac cta ccc caa acc gat gaa att aga gat gtt tta gac acg<br>Gly Pro Asp Leu Pro Gln Thr Asp Glu Ile Arg Asp Val Leu Asp Thr<br>500 505 510 | 1536 |
| ttc cgt gtc ata gca gaa ctt cca tct gac aac ttt gga gcc tac atc<br>Phe Arg Val Ile Ala Glu Leu Pro Ser Asp Asn Phe Gly Ala Tyr Ile<br>515 520 525 | 1584 |
| att tcg atg gca act gca ccg tct gat gtg ctg gca gtt gag ctt ctt<br>Ile Ser Met Ala Thr Ala Pro Ser Asp Val Leu Ala Val Glu Leu Leu<br>530 535 540 | 1632 |
| caa cgt gaa tgc aaa gtc agg aat cca tta aga gtc gtt ccg ttg ttt<br>Gln Arg Glu Cys Lys Val Arg Asn Pro Leu Arg Val Val Pro Leu Phe<br>545 550 555 560 | 1680 |
| gaa aag ctt gat gat ctt gag tct gct cct gct gca ttg gct cgg ttg<br>Glu Lys Leu Asp Asp Leu Glu Ser Ala Pro Ala Ala Leu Ala Arg Leu<br>565 570 575 | 1728 |

```
ttc tcc ata gac tgg tac att aac cgg atc gat ggg aag caa gaa gtt    1776
Phe Ser Ile Asp Trp Tyr Ile Asn Arg Ile Asp Gly Lys Gln Glu Val
            580                 585                 590 atg att gga tat tct gat tca gga aaa gat gct gga agg ttt tct gca    1824
Met Ile Gly Tyr Ser Asp Ser Gly Lys Asp Ala Gly Arg Phe Ser Ala
            595                 600                 605 gca tgg cag cta tat aag gct cag gag gac ctc atc aaa gtc gca cag    1872
Ala Trp Gln Leu Tyr Lys Ala Gln Glu Asp Leu Ile Lys Val Ala Gln
            610                 615                 620 aaa ttt ggt gtt aag cta acc atg ttc cac ggt cgt ggt gga act gtt    1920
Lys Phe Gly Val Lys Leu Thr Met Phe His Gly Arg Gly Gly Thr Val
625                 630                 635                 640 gga aga gga ggt gga cct acc cat ctt gct atc ttg tct caa cca cca    1968
Gly Arg Gly Gly Gly Pro Thr His Leu Ala Ile Leu Ser Gln Pro Pro
            645                 650                 655 gaa aca att cac gga tct ctt cgt gtg aca gtt caa ggt gaa gtt att    2016
Glu Thr Ile His Gly Ser Leu Arg Val Thr Val Gln Gly Glu Val Ile
            660                 665                 670 gaa cag tcg ttc ggt gag gaa cac ttg tgc ttt agg aca ctg caa cgt    2064
Glu Gln Ser Phe Gly Glu Glu His Leu Cys Phe Arg Thr Leu Gln Arg
            675                 680                 685 ttc act gct gct act cta gaa cat gga atg cgt ccc cca agc tct cca    2112
Phe Thr Ala Ala Thr Leu Glu His Gly Met Arg Pro Pro Ser Ser Pro
            690                 695                 700 aaa cca gaa tgg cgc gcc ttg atg gat cag atg gct gtc att gca act    2160
Lys Pro Glu Trp Arg Ala Leu Met Asp Gln Met Ala Val Ile Ala Thr
705                 710                 715                 720 gag gaa tac cgt tca att gtg ttc aag gaa cca cgt ttt gtt gag tat    2208
Glu Glu Tyr Arg Ser Ile Val Phe Lys Glu Pro Arg Phe Val Glu Tyr
            725                 730                 735 ttc cgt ctg gct aca cca gag atg gag tat ggt agg atg aac att gga    2256
Phe Arg Leu Ala Thr Pro Glu Met Glu Tyr Gly Arg Met Asn Ile Gly
            740                 745                 750 agt cga ccg gca aag aga agg cct agt gga ggc att gaa aca ctg cgt    2304
Ser Arg Pro Ala Lys Arg Arg Pro Ser Gly Gly Ile Glu Thr Leu Arg
            755                 760                 765 gcg ata cca tgg atc ttt gcc tgg aca cag aca agg ttt cat ctt cca    2352
Ala Ile Pro Trp Ile Phe Ala Trp Thr Gln Thr Arg Phe His Leu Pro
770                 775                 780 gta tgg ctg ggc ttt gga gca gca ttt aga caa gtt gtt cag aag gat    2400
Val Trp Leu Gly Phe Gly Ala Ala Phe Arg Gln Val Val Gln Lys Asp
785                 790                 795                 800 gtt aag aat ctc cat atg ctg caa gag atg tac aat caa tgg cct ttc    2448
Val Lys Asn Leu His Met Leu Gln Glu Met Tyr Asn Gln Trp Pro Phe
            805                 810                 815 ttt agg gtt aca att gat tta gtt gaa atg gtg ttt gcc aag ggt gac    2496
Phe Arg Val Thr Ile Asp Leu Val Glu Met Val Phe Ala Lys Gly Asp
            820                 825                 830 cct ggt att gca gca ctg aat gat agg ctc cta gtt tca aag gat ctg    2544
Pro Gly Ile Ala Ala Leu Asn Asp Arg Leu Leu Val Ser Lys Asp Leu
            835                 840                 845 tgg cca ttt ggg gaa caa ttg aga agc aaa tat gaa gaa act aag aaa    2592
Trp Pro Phe Gly Glu Gln Leu Arg Ser Lys Tyr Glu Glu Thr Lys Lys
850                 855                 860 ctc cta ctt cag gtg gct gca cac aag gaa gtt ctt gaa ggt gac ccc    2640
Leu Leu Leu Gln Val Ala Ala His Lys Glu Val Leu Glu Gly Asp Pro
865                 870                 875                 880 tac ttg aag caa aga ctc aga ctc cgt gat tcg tac att aca acc ctt    2688
Tyr Leu Lys Gln Arg Leu Arg Leu Arg Asp Ser Tyr Ile Thr Thr Leu
```

-continued

```
              885                 890                 895
aat gtt ttc caa gcc tac aca ttg aaa cgg atc cgc gat cca aac tac    2736
Asn Val Phe Gln Ala Tyr Thr Leu Lys Arg Ile Arg Asp Pro Asn Tyr
            900                 905                 910 aag gtg gag gtg cgc ccc cca ata tcg aaa gag tct gct gaa aca agt    2784
Lys Val Glu Val Arg Pro Pro Ile Ser Lys Glu Ser Ala Glu Thr Ser
        915                 920                 925 aaa cca gct gat gaa ctt gta aca ttg aat cca aca agt gaa tat gct    2832
Lys Pro Ala Asp Glu Leu Val Thr Leu Asn Pro Thr Ser Glu Tyr Ala
    930                 935                 940 cct ggt ttg gaa gac aca ctc att ctt acc atg aag ggt att gct gct    2880
Pro Gly Leu Glu Asp Thr Leu Ile Leu Thr Met Lys Gly Ile Ala Ala
945                 950                 955                 960 ggc atg cag aac act ggt taa                                        2901
Gly Met Gln Asn Thr Gly
                965
```

<210> SEQ ID NO 2
<211> LENGTH: 966
<212> TYPE: PRT
<213> ORGANISM: Medicago sativa

<400> SEQUENCE: 2

```
Met Ala Asn Lys Met Glu Lys Met Ala Ser Ile Asp Ala Gln Leu Arg
  1               5                  10                  15

Gln Leu Val Pro Ala Lys Val Ser Glu Asp Lys Leu Ile Glu Tyr
             20                  25                  30

Asp Ala Leu Leu Leu Asp Arg Phe Leu Asp Ile Leu Gln Asp Leu His
         35                  40                  45

Gly Glu Asp Leu Lys Asp Ser Val Gln Glu Val Tyr Glu Leu Ser Ala
     50                  55                  60

Glu Tyr Glu Arg Lys His Asp Pro Lys Lys Leu Glu Glu Leu Gly Asn
 65                  70                  75                  80

Leu Ile Thr Ser Phe Asp Ala Gly Asp Ser Ile Val Val Ala Lys Ser
                 85                  90                  95

Phe Ser His Met Leu Asn Leu Ala Asn Leu Ala Glu Glu Val Gln Ile
            100                 105                 110

Ala His Arg Arg Arg Asn Lys Leu Lys Lys Gly Asp Phe Arg Asp Glu
        115                 120                 125

Ser Asn Ala Thr Thr Glu Ser Asp Ile Glu Glu Thr Leu Lys Lys Leu
    130                 135                 140

Val Phe Asp Met Lys Lys Ser Pro Gln Glu Val Phe Asp Ala Leu Lys
145                 150                 155                 160

Asn Gln Thr Val Asp Leu Val Leu Thr Ala His Pro Thr Gln Ser Val
                165                 170                 175

Arg Arg Ser Leu Leu Gln Lys His Gly Arg Val Arg Asn Cys Leu Ser
            180                 185                 190

Gln Leu Tyr Ala Lys Asp Ile Thr Pro Asp Asp Lys Gln Glu Leu Asp
        195                 200                 205

Glu Ala Leu Gln Arg Glu Ile Gln Ala Ala Phe Arg Thr Asp Glu Ile
    210                 215                 220

Lys Arg Thr Pro Pro Thr Pro Gln Asp Glu Met Arg Ala Gly Met Ser
225                 230                 235                 240

Tyr Phe His Glu Thr Ile Trp Lys Gly Val Pro Lys Phe Leu Arg Arg
                245                 250                 255

Val Asp Thr Ala Leu Lys Asn Ile Gly Ile Asn Glu Arg Val Pro Tyr
```

```
                260                 265                 270
Asn Ala Pro Leu Ile Gln Phe Ser Ser Trp Met Gly Gly Asp Arg Asp
            275                 280                 285
Gly Asn Pro Arg Val Thr Pro Glu Val Thr Arg Asp Val Cys Leu Leu
        290                 295                 300
Ala Arg Met Met Ala Ala Asn Leu Tyr Tyr Ser Gln Ile Glu Asp Leu
305                 310                 315                 320
Met Phe Glu Leu Ser Met Trp Arg Cys Asn Asp Glu Leu Arg Val Arg
                325                 330                 335
Ala Glu Glu Leu His Arg Asn Ser Lys Lys Asp Glu Val Ala Lys His
            340                 345                 350
Tyr Ile Glu Phe Trp Lys Lys Ile Pro Leu Asn Glu Pro Tyr Arg Val
        355                 360                 365
Val Leu Gly Glu Val Arg Asp Lys Leu Tyr Arg Thr Arg Glu Arg Ser
        370                 375                 380
Arg Tyr Leu Leu Ala His Gly Tyr Cys Glu Ile Pro Glu Glu Ala Thr
385                 390                 395                 400
Phe Thr Asn Val Asp Glu Phe Leu Glu Pro Leu Glu Leu Cys Tyr Arg
                405                 410                 415
Ser Leu Cys Ala Cys Gly Asp Arg Ala Ile Ala Asp Gly Ser Leu Leu
            420                 425                 430
Asp Phe Leu Arg Gln Val Ser Thr Phe Gly Leu Ser Leu Val Arg Leu
        435                 440                 445
Asp Ile Arg Gln Glu Ser Asp Arg His Thr Asp Val Met Asp Ala Ile
        450                 455                 460
Thr Lys His Leu Glu Ile Gly Ser Tyr Gln Glu Trp Ser Glu Glu Lys
465                 470                 475                 480
Arg Gln Glu Trp Leu Leu Ser Glu Leu Ile Gly Lys Arg Pro Leu Phe
                485                 490                 495
Gly Pro Asp Leu Pro Gln Thr Asp Glu Ile Arg Asp Val Leu Asp Thr
            500                 505                 510
Phe Arg Val Ile Ala Glu Leu Pro Ser Asp Asn Phe Gly Ala Tyr Ile
        515                 520                 525
Ile Ser Met Ala Thr Ala Pro Ser Asp Val Leu Ala Val Glu Leu Leu
        530                 535                 540
Gln Arg Glu Cys Lys Val Arg Asn Pro Leu Arg Val Val Pro Leu Phe
545                 550                 555                 560
Glu Lys Leu Asp Asp Leu Glu Ser Ala Pro Ala Ala Leu Ala Arg Leu
                565                 570                 575
Phe Ser Ile Asp Trp Tyr Ile Asn Arg Ile Asp Gly Lys Gln Glu Val
            580                 585                 590
Met Ile Gly Tyr Ser Asp Ser Gly Lys Asp Ala Gly Arg Phe Ser Ala
        595                 600                 605
Ala Trp Gln Leu Tyr Lys Ala Gln Glu Asp Leu Ile Lys Val Ala Gln
        610                 615                 620
Lys Phe Gly Val Lys Leu Thr Met Phe His Gly Arg Gly Gly Thr Val
625                 630                 635                 640
Gly Arg Gly Gly Gly Pro Thr His Leu Ala Ile Leu Ser Gln Pro Pro
                645                 650                 655
Glu Thr Ile His Gly Ser Leu Arg Val Thr Val Gln Gly Glu Val Ile
            660                 665                 670
Glu Gln Ser Phe Gly Glu Glu His Leu Cys Phe Arg Thr Leu Gln Arg
        675                 680                 685
```

-continued

```
                Phe Thr Ala Ala Thr Leu Glu His Gly Met Arg Pro Pro Ser Ser Pro
                    690                 695                 700
                Lys Pro Glu Trp Arg Ala Leu Met Asp Gln Met Ala Val Ile Ala Thr
                705                 710                 715                 720
                Glu Glu Tyr Arg Ser Ile Val Phe Lys Glu Pro Arg Phe Val Glu Tyr
                                725                 730                 735
                Phe Arg Leu Ala Thr Pro Glu Met Glu Tyr Gly Arg Met Asn Ile Gly
                            740                 745                 750
                Ser Arg Pro Ala Lys Arg Arg Pro Ser Gly Gly Ile Glu Thr Leu Arg
                        755                 760                 765
                Ala Ile Pro Trp Ile Phe Ala Trp Thr Gln Thr Arg Phe His Leu Pro
                    770                 775                 780
                Val Trp Leu Gly Phe Gly Ala Ala Phe Arg Gln Val Val Gln Lys Asp
                785                 790                 795                 800
                Val Lys Asn Leu His Met Leu Gln Glu Met Tyr Asn Gln Trp Pro Phe
                                805                 810                 815
                Phe Arg Val Thr Ile Asp Leu Val Glu Met Val Phe Ala Lys Gly Asp
                            820                 825                 830
                Pro Gly Ile Ala Ala Leu Asn Asp Arg Leu Leu Val Ser Lys Asp Leu
                        835                 840                 845
                Trp Pro Phe Gly Glu Gln Leu Arg Ser Lys Tyr Glu Glu Thr Lys Lys
                    850                 855                 860
                Leu Leu Leu Gln Val Ala Ala His Lys Glu Val Leu Glu Gly Asp Pro
                865                 870                 875                 880
                Tyr Leu Lys Gln Arg Leu Arg Leu Arg Asp Ser Tyr Ile Thr Thr Leu
                                885                 890                 895
                Asn Val Phe Gln Ala Tyr Thr Leu Lys Arg Ile Arg Asp Pro Asn Tyr
                            900                 905                 910
                Lys Val Glu Val Arg Pro Pro Ile Ser Lys Glu Ser Ala Glu Thr Ser
                        915                 920                 925
                Lys Pro Ala Asp Glu Leu Val Thr Leu Asn Pro Thr Ser Glu Tyr Ala
                    930                 935                 940
                Pro Gly Leu Glu Asp Thr Leu Ile Leu Thr Met Lys Gly Ile Ala Ala
                945                 950                 955                 960
                Gly Met Gln Asn Thr Gly
                                965

<210> SEQ ID NO 3
<211> LENGTH: 3372
<212> TYPE: DNA
<213> ORGANISM: Corynebacterium glutamicum

<400> SEQUENCE: 3
cagacccgca agtcccttgc tggcctggat gctgctgagc tggccaacac cgttatcgcg     60
tatgagccag tgtgggctat cggcactggc aaggttgctt ccgcggctga cgctcaggaa    120
gtgtgcaagg ctatccgcgg tctgatcgtg gagcttgcag cgacgaggt cgctgagggc    180 ctgcgtattc tttacggtgg ttctgttaag gcagaaaccg tcgcagagat cgtcggtcag    240
cctgacgtcg acgcggact tgtcggtggc gcttccctcg acggtgaagc attcgccaag    300
ctggctgcca acgctgcgag cgttgcttaa agtacagagc tttaaagcac agccttaaag    360
cacagcctta agcacaagc actgtagaag tgcggttttg atgagcccat gaaagccatc    420
gaaatcaatc gcccagctaa acacctgttt tgctgggtga tttttttatct catgcacgcc    480
```

-continued

```
aacacccca atgtgaaaga gtgtttaaag tagttatgac tgattttta cgcgatgaca      540
tcaggttcct cggtcaaatc ctcggtgagg taattgcgga acaagaaggc caggaggttt      600
atgaactggt cgaacaagcg cgcctgactt cttttgatat cgccaagggc aacgccgaaa      660
tggatagcct ggttcaggtt ttcgacggca ttactccagc caaggcaaca ccgattgctc      720
gcgcattttc ccacttcgct ctgctggcta acctggcgga agacctctac gatgaagagc      780
ttcgtgaaca ggctctcgat gcaggcgaca ccctccgga cagcactctt gatgccacct       840
ggctgaaact caatgagggc aatgttggcg cagaagctgt ggccgatgtg ctgcgcaatg      900
ctgaggtggc gccggttctg actgcgcacc caactgagac tcgccgccgc actgttttttg    960
atgcgcaaaa gtggatcacc acccacatgc gtgaacgcca cgctttgcag tctgcggagc     1020
ctaccgctcg tacgcaaagc aagttggatg agatcgaaaa gaacatccgc cgtcgcatca     1080
ccattttgtg gcagaccgcg ttgattcgtg tggcccgccc acgtatcgag gacgagatcg     1140
aagtagggct gcgctactac aagctgagcc ttttggaaga gattccacgt atcaaccgtg     1200
atgtggctgt tgagcttcgt gagcgtttcg gcgaggatgt tcctttgaag cccgtggtca     1260
agccaggttc ctggattggt ggagaccacg acggtaaccc ttatgtcacc gcggaaacag     1320
ttgagtattc cactcaccgc gctgcggaaa ccgtgctcaa gtactatgca cgccagctgc     1380
attccctcga gcatgagctc agcctgtcgg accgcatgaa taaggtcacc ccgcagctgc     1440
ttgcgctggc agatgcaggg cacaacgacg tgccaagccg cgtggatgag ccttatcgac     1500
gcgccgtcca tggcgttcgc ggacgtatcc tcgcgacgac ggccgagctg atcggcgagg     1560
acgccgttga gggcgtgtgg ttcaaggtct ttactccata cgcatctccg gaagaattct     1620
taaacgatgc gttgaccatt gatcattctc tgcgtgaatc caaggacgtt ctcattgccg     1680
atgatcgttt gtctgtgctg atttctgcca tcgagagctt tggattcaac ctttacgcac     1740
tggatctgcg ccaaaactcc gaaagctacg aggacgttct caccgagctt tttgagcgcg     1800
cccaagtcac cgcaaactac cgcgagctgt ctgaagcaga gaagcttgag gtgctgctga     1860
aggaactgcg cagccctcgt ccgctgatcc cgcacggttc agatgaatac agcgaggtca     1920
ccgaccgcga gctcggcatc ttccgcaccg catctgaagc tgttaagaaa tttgggccac     1980
ggatggtgcc tcactgcatc atctccatgg catcatcggt caccgatgtg ctggagccaa     2040
tggtgttgct caaggaattc ggactcatcg cagccaacgg cgacaaccca cgcggcaccg     2100
tcgatgtcat cccactgttc gaaaccatcg aagatctcca ggccggcgcc ggaatcctcg     2160
acgaactgtg gaaaattgat ctctaccgca actacctcct gcagcgcgac aacgtccagg     2220
aagtcatgct cggttactcc gattccaaca aggatggcgg atatttctcc gcaaactggg     2280
cgctttacga cgcggaactg cagctcgtcg aactatgccg atcagccggg gtcaagcttc     2340
gcctgttcca cggccgtggt ggcaccgtcg gccgcggtgg cggaccttcc tacgacgcga     2400
ttcttgccca gcccaggggg gctgtccaag gttccgtgcg catcaccgag cagggcgaga     2460
tcatctccgc taagtacggc aaccccgaaa ccgcgcgccg aaacctcgaa gctctggtct     2520
cagccacgct tgaggcatcg cttctcgacg tctccgaact caccgatcac caacgcgcgt     2580
acgacatcat gagtgagatc tctgagctca gcttgaagaa gtacgcctcc ttggtgcacg     2640
aggatcaagg cttcatcgat tacttcaccc agtccacgcc gctgcaggag attggatccc     2700
tcaacatcgg atccaggcct tcctcacgca agcagacctc ctcggtggaa gatttgcgag     2760
ccatcccatg ggtgctcagc tggtcacagt ctcgtgtcat gctgccaggc tggtttggtg     2820
tcggaaccgc attagagcag tggattggcg aaggggagca ggccacccaa cgcattgccg     2880
```

```
                                                                -continued agctacaaac actcaatgag tcctggccat ttttcacctc agtgttggat aacatggctc    2940
aggtgatgtc caaggcagag ctgcgtttgg caaagctcta cgccgacctc atcccagata    3000
gggaagtagc cgagcgcgtc tattccgtca tccgcgagga atacttcctg accaagaaga    3060
tgttctgcgt aatcaccggt tctgatgatc tgcttgatga caacccactt ctcgcacgct    3120
ctgtccagcg ccgttaccct tacctgcttc cactcaacgt gatccaggta gagatgatgc    3180
gacgctaccg aaaaggcgac caaagcgagc aagtatcccg caacatccag ctgaccatga    3240
acggtctttc cactgcgctg cgcaactccg gctagtccag ccggctgggt agtactcgtg    3300
tatactgtct aaagttattc gaaatcaggt gggcataagg ttcacctggg ttctcaaacg    3360
gcaaaggaac at                                                       3372

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
gttggtgagc cactggaaat ccgtg                                            25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
gatgtcatcg cgtaaaaaat cagtc                                            25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
cactgcgctg cgcaactcta gatag                                            25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
gaccaccacc ttgccgaaat cttgg                                            25
```

REGULATION OF CARBON ASSIMILATION

CROSS-REFERENCE TO RELATED APPLICATIONS

This application claims priority benefit of U.S. Provisional Application No. 60/141,001, filed Jun. 29, 1999, which is hereby incorporated by reference in its entirety.

BACKGROUND OF THE INVENTION

1. Field of the Invention

This invention relates to a polypeptide having phosphoenolpyruvate carboxylase activity which does not require acetyl coenzyme A for activation and is desensitized to feedback inhibition by aspartic acid, and to genes coding for this polypeptide. The invention also relates to recombinant DNA molecules containing these genes, to bacteria transformed with these genes, and to methods of producing amino acids using the transformed bacteria.

2. Related Art

Phosphoenolpyruvate (PEP) carboxylase (EC 4.1.1.31) is an enzyme which is found in almost all bacteria and all plants. PEP carboxylase catalyzes the condensation reaction between the three carbon glycolytic intermediate PEP and carbon dioxide resulting in the formation of the four carbon oxaloacetate (OAA), a metabolic intermediate common to the tricarboxylic acid (TCA) cycle and to L-aspartic acid biosynthesis. The TCA cycle requires continuous replenishment of $C_4$ molecules in order to replace the intermediates withdrawn for amino acid biosynthesis, and by playing an anaplerotic role in supplying OAA to the TCA cycle, the biotin-independent PEP carboxylase aids in fulfilling this function.

OAA is a very important substrate for the production of cell metabolites such as amino acids, especially the glutamate family, i.e., glutamate, arginine and proline, and the aspartate family, i.e., aspartate, lysine, methionine, threonine and isoleucine. By catalyzing the reaction which results in the formation of OAA, PEP carboxylase plays an important role in supplying organic acids by metabolic processes. For example, fermentive production of succinic acid from glucose by *Escherichia coli* was significantly increased by the over-expression of PEP carboxylase. See Millard, C., et al., *Appl. Environ. Microbiol.* 62:1808–1810 (1996). Accordingly, PEP carboxylase also plays an important role in the production of amino acids which are formed from glutamate and aspartate.

The amino acid is a compound which universally exists in cells as components of proteins. However, for the sake of economic energy metabolism and substance metabolism, its production is strictly controlled. This control is principally feedback control, in which the final product of a metabolic pathway inhibits the activity of an enzyme which catalyzes an earlier step of the pathway. PEP carboxylase also undergoes various regulations in expression of its activity.

For example, in the case of PEP carboxylase of microorganisms belonging to the genus Brevibacterium, Corynebacterium or the genus Escherichia, PEP carboxylase activity is inhibited by aspartic acid. See e.g., Mori, M., et al., *J. Biochem.* 98:1621–1630 (1985); O'Regan, M., et al., *Gene* 77:237–251 (1989). Therefore, the aforementioned amino acid biosynthesis, in which PEP carboxylase participates, is also inhibited by aspartic acid. However, PEP carboxylase activities from Corynebacterium microorganisms having decreased sensitivity to aspartic acid have been described. See Eikmanns, B. J., et al., *Mol. Gen. Genet.* 218:330–339 (1989).

In addition to being allosterically inhibited by aspartic acid, acetyl co-enzyme A (acetyl-CoA) is an allosteric activator of PEP carboxylase from *Brevibacterium flavum* and *Escherichia coli*, for example. See Mori, M., et al., *J. Biochem.* 98:1621–1630 (1985); Morikawa, M., et al., *J. Biochem.* 81:1473–1485 (1977). PEP carboxylases from other organisms that are not regulated by aspartic acid or acetyl-CoA have been reported. See Valle, F., et al., *J. Indus. Microbiol.* 17:458–462 (1996); O'Regan, M., et al., *Gene* 77:237–251 (1989); Vance, C., et al., *Plant Physiol.* 75:261–264 (1984).

Since the anaplerotic enzyme PEP carboxylase is critical to the maintenance of an optimal pool of OAA, and consequently determines the biosynthetic levels of amino acids deriving from OAA, one way of improving amino acid production by fermentation would be to manipulate the corresponding ppc gene. For example, the amplification of the ppc gene from *Brevibacterium lactofermentum* has been shown to improve the production of proline and threonine. See Sano, K., et al., *Agric. Biol. Chem.* 51:597–599 (1987).

Various techniques have been developed for efficient production in amino acid fermentation by using mutant strains converted to be insensitive to feedback control. However, there has been no report of utilizing a PEP carboxylase derived from a plant for fermentative production of amino acids of the aspartic acid or glutamic acid families or of utilizing a ppc gene derived from a coryneform bacterium which is integrated into microbial chromosomal DNA for fermentative production of amino acids of the same families in which the PEP carboxylase is not substantially regulated by acetyl-CoA or aspartic acid.

U.S. Pat. No. 4,757,009 (Sano et al.; Ajinomoto Company) discloses a process for producing an amino acid by fermentation which comprises cultivating in a culture medium a Corynebacterium or Brevibacterium strain carrying a recombinant DNA molecule comprising a plasmid having operationally inserted therein a gene coding for PEP carboxylase, wherein the gene is a chromosomal gene isolated from a Corynebacterium or a Brevibacterium strain carrying a PEP carboxylase gene and has a chromosomal gene coding for an amino acid, and isolating the amino acid from the culture medium. The Corynebacterium or Brevibacterium strain from which the gene coding for PEP carboxylase is isolated is a strain which exhibits weakened feedback inhibition by aspartic acid.

European Patent No. 358,940 (Bachmann et al.; Degussa Aktiengesellschaft) discloses a plasmid pDM6 that is introduced into *Corynebacterium glutamicum* DM58-1, which is deposited at the Deutsche Sammlung von Mikroorganismen (DSM) under DSM 4697, wherein the plasmid contains a genetic sequence comprising information coding for the production of a protein having PEP carboxylase activity. The ppc gene is isolated from a genomic bank of *Corynebacterium glutamicum* ATCC 13032, and the PEP carboxylase is not stimulated by acetyl-CoA. Also disclosed is a method of producing L-lysine, L-threonine, and L-isoleucine by fermentation which comprises culturing in an appropriate medium a host bacterium belonging to the genus Corynebacterium or Brevibacterium which contains plasmid pDM6, and recovering the L-amino acid from the medium.

U.S. Pat. No. 5,876,983 (Sugimoto et al.; Ajinomoto Company) discloses a method of producing an amino acid which comprises selecting a microorganism of the genus Escherichia containing a DNA sequence encoding a mutant PEP carboxylase desensitized to feedback inhibition by aspartic acid by growing Escherichia microorganisms in the presence of a wild-type PEP carboxylase inhibitor selected from the group consisting of 3-bromopyruvate, aspartic acid-β-hydrazide and DL-threo-β-hydroxyaspartic acid; culturing a microorganism of the genus Escherichia or coryneform bacteria transformed with the DNA sequence encoding a mutant PEP carboxylase in a suitable medium; and separating from the medium an amino acid selected from the group consisting of L-lysine, L-threonine, L-methionine, L-isoleucine, L-glutamic acid, L-arginine and L-proline.

Although there are many examples of culturing amino acid-producing bacteria by recombinant DNA techniques, high levels of amino acid productivity are not always achieved. Therefore, a need still continues to exist for a method of producing amino acids by fermentation in high titre and yields. A PEP carboxylase that is not substantially regulated by acetyl-CoA or aspartic acid could improve carbon flow from the three carbon intermediate PEP to the four carbon intermediate OAA. The improved flow could contribute to compounds derived from OAA and increase amino acid biosynthesis.

SUMMARY OF THE INVENTION

Accordingly, the present invention relates to a DNA fragment comprising a gene encoding a polypeptide having PEP carboxylase activity, wherein the gene is capable of being expressed in a host microorganism, and wherein the polypeptide does not require acetyl-CoA for activation and is desensitized to feedback inhibition by aspartic acid.

The present invention also relates to a recombinant DNA molecule comprising a plasmid and a gene encoding a polypeptide having PEP carboxylase activity operationally inserted therein, wherein the recombinant DNA molecule is capable of propagating and the gene is capable of being expressed in a host microorganism comprising the genus Escherichia, Corynebacterium and Brevibacterium, and wherein the polypeptide does not require acetyl-CoA for activation and is desensitized to feedback inhibition by aspartic acid.

The present invention further relates to a host microorganism belonging to the genus Escherichia, Corynebacterium or Brevibacterium transformed with a DNA fragment comprising a gene encoding a polypeptide having PEP carboxylase activity, wherein the gene is derived from a plant belonging to the class Monocotyledonae or Dicotyledonae or from a microorganism belonging to the genus Corynebacterium or Brevibacterium, wherein the polypeptide does not require acetyl-CoA for activation and is desensitized to feedback inhibition by aspartic acid, and wherein the host microorganism transformed with the DNA fragment expresses the gene.

In another aspect of the present invention there is provided a method of producing an amino acid by fermentation. The method comprises cultivating a host microorganism belonging to the genus Escherichia, Corynebacterium or Brevibacterium in a suitable medium and isolating from the culture medium an amino acid, wherein the host microorganism is transformed with a DNA fragment comprising a gene encoding a polypeptide having PEP carboxylase activity, wherein the host microorganism expresses the gene, and wherein the polypeptide does not require acetyl-CoA for activation and is desensitized to feedback inhibition by aspartic acid.

In addition, the present invention relates to a method of selecting a DNA fragment comprising a gene encoding a polypeptide having PEP carboxylase activity wherein the polypeptide does not require acetyl-CoA for activation and is desensitized to feedback inhibition by aspartic acid, to a method of increasing the rate of conversion of PEP to OAA, to a method of recycling carbon in a fermentation process, to a method of assimilating carbon in a fermentation process which does not require biotin, to a method of increasing the production of organic acids in a fermentation process, and to a method of increasing the production of amino acids in a fermentation process.

DETAILED DESCRIPTION OF THE PREFERRED EMBODIMENTS

Figure 1:
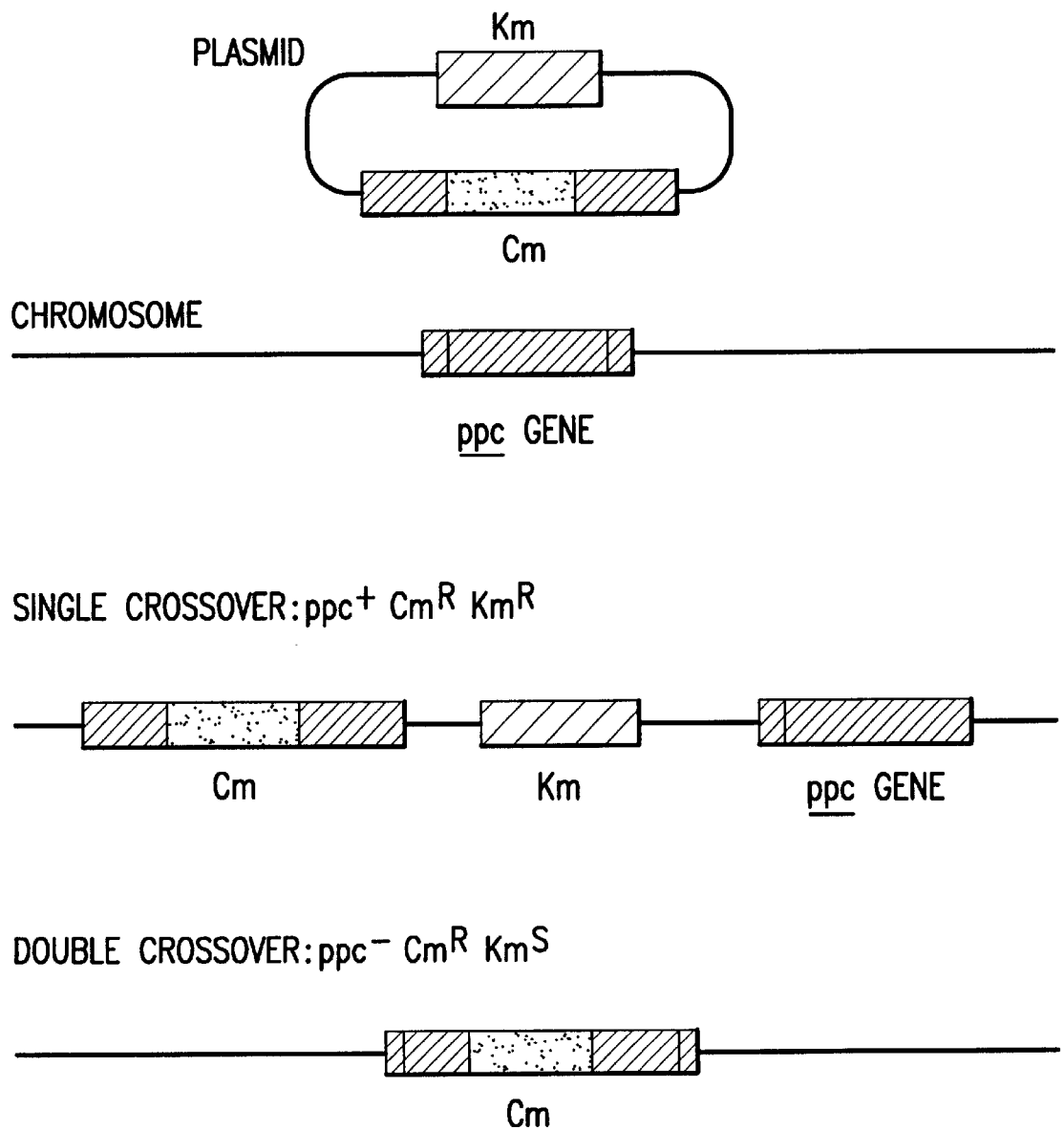
FIG. 1 is a diagram of a strategy for gene replacement.

Before describing the invention in detail, several terms used in the specification will be defined.

"Activator," as used herein, includes both a substance necessary for the polypeptide to become active in the first place, as well as a substance which merely accentuates activity.

"Amino acids" as used herein refer to the naturally occurring L amino acids (alanine, arginine, aspartic acid, asparagine, cystine, glutamic acid, glutamine, glycine, histidine, isoleucine, leucine, lysine, methionine, proline, phenylalanine, serine, threonine, tryptophan, tyrosine, and valine).

"Chimeric gene" refers to a gene comprising heterogeneous regulatory and coding sequences. It is a hybrid gene produced by recombinant DNA technology.

"DNA fragment" refers to a fraction of a deoxyribonucleic acid molecule.

"Expression," as used herein, is intended to mean the production of the protein product encoded by a gene.

"Gene" refers to a nucleic acid fragment that expresses a specific protein, including regulatory sequences preceding (5' non-coding) and following (3' non-coding) the coding region. It is a discrete chromosomal region comprising regulatory DNA sequences responsible for the control of expression, i.e., transcription and translation, and for a coding sequence which is transcribed and translated to give a distinct polypeptide.

"Host microorganism" means the microorganism that is transformed with the introduced genetic material.

"Inhibition" includes both the reduction of activity of the polypeptide and the complete lack of activity as well.

"Isolated" as used herein means that the material is removed from its original environment (e.g., the natural environment if it is naturally occurring).

"Polypeptide" or "protein" as used herein refers to a molecule composed of monomers (amino acids) linearly linked by amide bonds (also known as peptide bonds). It indicates a molecular chain of amino acids and does not refer to a specific length of the product. Thus, peptides, oligopeptides and proteins are included within the definition of polypeptide. This term is also intended to refer to post-expression modifications of the polypeptide, for example, glycosolations, acetylations, phosphorylations, and the like. A recombinant or derived polypeptide is not necessarily translated from a designated nucleic acid sequence. It may also be generated in any manner, including chemical synthesis or expression of a recombinant expression system.

"Regulatory sequences" refer to nucleotide sequences located upstream (5'), within, and/or downstream (3') to a coding sequence, which control the transcription and/or expression of the coding sequences, potentially in conjunction with the protein biosynthetic apparatus of the cell.

"Synthetic DNA" refers to a nucleic acid molecule produced in whole or in part by chemical synthesis methods.

"Transformation" herein refers to the transfer of a foreign gene into a host cell either as part of the host cell genomic DNA or as an independent molecule, and its genetically stable inheritance.

In one aspect of the invention there is provided a DNA fragment comprising a gene encoding a polypeptide having PEP carboxylase activity, wherein the gene is capable of being expressed in a host microorganism, and wherein the polypeptide does not require acetyl-CoA for activation and is desensitized to feedback inhibition by aspartic acid.

The ppc gene, which encodes the enzyme PEP carboxylase, may be any one provided that it is a gene encoding for the PEP carboxylase of a plant belonging to the class Monocotyledonae or Dicotyledonae or of a microorganism belonging to the genus Brevibacterium or Corynebacterium, and provided the expressed polypeptide does not require acetyl-CoA for activation and is substantially desensitized to feedback inhibition by aspartic acid. The ppc gene is preferably determined for its base sequence and cloned. When it has not been cloned, a DNA fragment containing the gene can be amplified and isolated by using the PCR method and the like, followed by using a suitable vector to achieve cloning. Preferred donors of the ppc gene are strains which exhibit weakened feedback inhibition by aspartic acid. Such strains are recognized as being resistant to aspartic acid-antagonistic inhibitors.

PEP carboxylase is a key enzyme of photosynthesis in $C_4$ plants. It is specifically localized in the cytosol of mesophyll cells and is regulated by a phosphorylation/dephosphoylation process. See Giglioli-Guivarc'h, N., et al., *Cytometry* 23:241–249 (1996). In addition, PEP carboxylase plays a crucial role in the assimilation of $CO_2$ during symbiotic $N_2$ fixation in legume root nodules. See Pathirana, S., et al., *Plant J.* 12:293–304 (1997).

In one embodiment, the DNA fragment containing a gene encoding a polypeptide having PEP carboxylase activity is derived from a plant belonging to the class Monocotyledonae or Dicotyledonae. In a preferred embodiment, the DNA fragment is derived from an alfalfa plant. Most preferably, the DNA fragment is derived from a *Medicago sativa* strain.

It has been shown that PEP carboxylase activity from a strain of *Medicago sativa* was not substantially inhibited by L-aspartic acid. See Vance, C. P., et al., *Plant Physiol.* 75:261–264 (1984). Further, the native ppc nucleotide sequence from *Medicago sativa* is known (Pathirana, S., et al., *Plant Molecular Biology* 20:437–450 (1992)) and provided in SEQ ID NO:1, and the amino acid sequence of the native PEP carboxylase encoded thereby is provided in SEQ ID NO:2. Since these sequences are known, primers may be designed and synthesized based on the nucleotide sequences, and then the genes may be obtained by PCR, using the messenger RNA as a template.

Post-translational regulation of plant PEP carboxylase is achieved, for example, through phosphorylation of the protein. See Jiao, J. A., et al., *Arch. Biochem. Biophys.* 269:526–535 (1989); Duff, S. M., et al., *Eur. J. Biochem.* 228:92–95 (1995). Alfalfa PEP carboxylase contains several conserved sequences, one of which is proposed to be involved in phosphorylation (MASIDAQLR, residues 8 to 16). See Pathirana, S. M., et al., *Plant Molecular Biology* 20:437–450 (1992).

In another preferred embodiment, the DNA fragment containing a gene encoding a polypeptide having PEP carboxylase activity which is derived from a plant belonging to the class Monocotyledonae or Dicotyledonae is modified by one or more nucleotide substitutions, deletions and/or insertions. Most preferably, the modification comprises deleting the nucleotides encoding the amino acid sequence: Met-Ala-Ser-Ile-Asp-Ala-Gln-Leu-Arg.

In another embodiment, the DNA fragment containing a gene encoding a polypeptide having PEP carboxylase activity is derived from a microorganism belonging to the genus Brevibacterium or Corynebacterium. In a preferred embodiment, the DNA fragment is derived from a *Corynebacterium glutamicum* strain. The native ppc nucleotide sequence of *Corynebacterium glutamicum* is shown in SEQ ID NO:3.

It is to be understood that the number of amino acids in the active PEP carboxylase molecule of the present invention may vary, and all amino acid sequences derived from an alfalfa plant or a Corynebacterium strain that have PEP carboxylase activity and the desired de-regulatory characteristics are contemplated as being included in the present invention. Polypeptide sequences which differ from each other only by conservative substitutions are included as well. Such conservative substitutions consist of a substitution of one amino acid at a given position in the sequence for another amino acid of the same class. One or more non-conservative amino acid substitutions, deletions and/or insertions, located at positions of the sequence that do not alter the polypeptide to the extent that the biological activity of the polypeptide is destroyed, are also included.

Modifications to the sequence, such as deletions, insertions, and/or substitutions in the sequence which produce silent changes that do not substantially affect the functional properties of the resulting PEP carboxylase protein molecule are also contemplated. For example, an alteration in the gene sequence which reflects the degeneracy of the genetic code, or which results in the production of a chemically equivalent amino acid at a given site, are contemplated.

It is therefore understood that the invention encompasses more than the specific exemplary sequences. Each of the proposed modifications is well within the routine skill in the art, as is determination of retention of biological activity of the encoded products.

In another embodiment, the DNA fragment containing a gene encoding a polypeptide having PEP carboxylase activity is a chimeric gene comprising an incomplete PEP carboxylase nucleotide sequence derived from a microorganism belonging to the genus Brevibacterium or Corynebacterium and an incomplete PEP carboxylase nucleotide sequence derived from a plant belonging to the class Monocotyledonae or Dicotyledonae. Together, the two incomplete sequences form a complete chimeric ppc gene capable of expressing a polypeptide having PEP carboxylase activity in which the polypeptide does not require acetyl coenzyme A for activation and is desensitized to feedback inhibition by aspartic acid.

In a preferred embodiment, one incomplete PEP carboxylase nucleotide sequence is derived from a microorganism belonging to the genus Corynebacterium, and the other incomplete PEP carboxylase nucleotide sequence is derived from an alfalfa plant. Most preferably, one incomplete PEP carboxylase nucleotide sequence is derived from a *Corynebacterium glutamicum* strain, and the other incomplete PEP carboxylase nucleotide sequence is derived from a *Medicago sativa* strain.

In another embodiment, the DNA fragment is complementary DNA (cDNA), genomic DNA or synthetic DNA. A DNA fragment of the present invention encoding PEP carboxylase can readily be obtained in a variety of ways, including, without limitation, chemical synthesis, cDNA or genomic library screening, expression library screening, and/or PCR amplification of cDNA. These methods and others useful for isolating such DNA are set forth, for example, by Sambrook et al. (*Molecular Cloning: A Laboratory Manual*, Cold Spring Harbor Laboratory Press, Cold Spring Harbor (1989)), by Ausubel et al., eds. (*Current Protocols in Molecular Biology*, Current Protocols Press (1994)), and by Berger and Kimmel (*Methods in Enzymology: Guide to Molecular Cloning Techniques*, Vol. 152, Academic Press, Inc., San Diego (1987)).

Isolation of the ppc gene can be conducted, for example, by the following method. Although the following example refers to Corynebacterium for simplicity, it is to be recognized that bacteria from the genus Brevibacterium can likewise be used. First, a chromosomal gene is extracted from a Corynebacterium strain carrying a ppc gene (utilizing, for example, the method of H. Saito and K. Miura, *Biochem. Biophys. Acta* 72:619 (1963)). The gene is cleaved with an appropriate restriction enzyme and then sub-cloned onto a plasmid shuttle vector capable of propagating in coryneform bacteria or in *E. coli*.

To cleave chromosomal genes, a wide variety of restriction enzymes can be employed by controlling the degree of cleavage, for example, by controlling the time of the cleavage reaction, the temperature, etc. Cleavage of DNA by restriction enzymes is well understood by those skilled in the art and need not be set forth here in detail.

A PEP carboxylase-deficient mutant of coryneform bacteria or *E. coli* is transformed with the resulting recombinant DNA. Transformants thus obtained can be selected and isolated by conventional methods based on characteristics possessed by the vector DNA and/or the recipient. For example, bacterial strains which come to possess PEP carboxylase activity are isolated, and a ppc gene can be isolated therefrom.

When the microorganism transformed with the DNA fragment of the present invention as described above is cultivated, and the DNA sequence is expressed, then an enzyme which does not require acetyl-CoA for activation and is substantially desensitized to aspartic acid inhibition may be obtained. It becomes apparent, by measuring PEP carboxylase activity in the absence and/or presence of acetyl-CoA, for example, whether or not the enzyme requires acetyl-CoA as an activator. It also becomes apparent, by measuring the PEP carboxylase activity in the presence and/or absence of aspartic acid in an enzyme reaction system, for example, whether or not the enzyme thus obtained is substantially inhibited by aspartic acid.

It is possible for the measurement of the enzyme activity to use a spectrometric method (Yoshinage, T., et al., *J. Biochem.* 68:747–750 (1970)) and the like. For example, when the enzyme assay is measured in a continuous or kinetic mode while the reaction is occurring, the reaction can be measured spectrophotometrically by following the decrease in the absorbance (usually at 340 nanometers).

In another aspect of the invention there is provided a method of selecting a DNA fragment comprising a gene encoding a polypeptide having PEP carboxylase activity wherein the polypeptide does not require acetyl-CoA for activation and is desensitized to feedback inhibition by aspartic acid. The method comprises extracting a chromosomal gene from a Corynebacterium strain carrying a ppc gene, cleaving the chromosomal gene with an appropriate restriction enzyme, ligating the ppc gene with a plasmid vector capable of propagating in Corynebacterium, transforming a Corynebacterium strain in which the ppc and pyc genes are nonfunctional, isolating strains which show superior growth on minimal medium with glucose as the only carbon source, and isolating a DNA fragment from the strain.

Pyruvate carboxylase (EC 6.4.1.1) is an important anaplerotic enzyme that replenishes OAA, which is consumed for biosynthesis during growth, from pyruvate and is used in lysine and glutamic acid production in industrial fermentations. In addition to PEP carboxylase, the biotin-dependent pyruvate carboxylase encoded by the pyc gene has recently been found to be an anaplerotic enzyme in *Corynebacterium glutamicum*. Inactivation of both the ppc and the pyc gene in *Corynebacterium glutamicum* led to the inability of the microorganism to grow on glucose. See Peters-Wendisch, P., el al., *Microbiology* 144:915–27 (1998). By inactivating both the ppc and the pyc genes, a DNA fragment containing a ppc gene of the invention that was cloned into a replicating plasmid can be identified by the ability of a strain to show growth on minimal medium with glucose as the only carbon source.

In another embodiment, inhibitors of PEP carboxylase activity are also added to the medium. For example, an analog of aspartic acid may be added.

The analog compound preferably exhibits a growth inhibitory action against a microorganism belonging to the genus Corynebacterium which produces a wild-type PEP carboxylase, the aforementioned growth inhibitory action is recovered by existence of L-glutamic or L-aspartic acid, and the analog compound inhibits wild-type PEP carboxylase activity. If a strain being resistant to the analog compound is selected from a microorganism belonging to the genus Corynebacterium, it is much more likely that a host microorganism which produces PEP carboxylase with desensitized feedback inhibition by aspartic acid will be obtained.

In another embodiment, strains are isolating which show an increased production of an amino acid derived from OAA. Such amino acids include aspartate, lysine, methionine, threonine and isoleucine. In addition, strains can be grown on minimal medium in the absence of acetyl-CoA, and the PEP carboxylase activity can be measured.

In another aspect of the invention there is provided a recombinant DNA molecule comprising a plasmid and a gene encoding a polypeptide having PEP carboxylase activity operationally inserted therein, wherein the recombinant DNA molecule is capable of propagating and the gene is capable of being expressed in a host microorganism comprising the genus Escherichia, Corynebacterium and Brevibacterium, and wherein the polypeptide does not require acetyl-CoA for activation and is desensitized to feedback inhibition by aspartic acid.

The plasmid vector used in the present invention can be any vector as long as it can be propagated in cells of bacteria from Escherichia, Corynebacterium or Brevibacterium. The vector DNA is cleaved by the same restriction enzyme used for cleavage of the chromosomal gene or is connected to an oligonucleotide having a complementary base sequence at the respective terminals of the chromosomal DNA cleavage fragment and the cleaved vector DNA. The plasmid vector and the chromosomal gene-containing fragment are then subjected to a ligation reaction. When a gene is inserted by this or any other method in the sense direction and in proper reading frame so that the PEP carboxylase enzyme is expressed when the plasmid is transcribed and translated by the genetic machinery of a cell in which the plasmid is inserted, the gene is said to be "operationally inserted" into the plasmid vector.

In a preferred embodiment, the gene encoding the polypeptide having PEP carboxylase activity is derived from an alfalfa plant. Most preferably, the gene is derived from a *Medicago sativa* strain. In another preferred embodiment, the gene is modified by one or more nucleotide substitutions, deletions and/or insertions. Most preferably, the modification comprises deleting the nucleotides encoding the amino acid sequence: Met-Ala-Ser-Ile-Asp-Ala-Gln-Leu-Arg.

In another aspect of the invention there is provided a host microorganism transformed with a DNA fragment of the present invention containing a gene encoding a polypeptide having PEP carboxylase activity. As the host, microorganisms utilized for the production of L-amino acids may be used, for example, those belonging to the genus Brevibacterium, the genus Corynebacterium, the genus Bacillus, the genus Escherichia, the genus Seratia, the genus Providencia, and the genus Arthrobacter.

In a preferred embodiment, the DNA fragment containing the ppc gene is expressed in a host microorganism belonging to the genus Escherichia, Corynebacterium or Brevibacterium. As the host, there may be exemplified microorganisms belonging to the genus Escherichia, for example, *Escherichia coli*, preferably L-lysine-producing *Escherichia coli*, coryneform bacteria, preferably L-lysine-producing strains, and the like. The coryneform bacteria referred to in the present invention is a group of microorganisms which are aerobic Gram-positive non-acid-fast rods having no spore-forming ability, including bacteria belonging to the genus Corynebacterium, bacteria belonging to the genus Brevibacterium having been hitherto classified into the genus Brevibacterium but being united as bacteria belonging to the genus Corynebacterium at present, and bacteria belonging to the genus Brevibacterium closely related to bacteria belonging to the genus Corynebacterium.

In one embodiment, when the DNA fragment is derived from a plant from the class Monocotyledonae or Dicotyledonae, the host microorganism may be transformed with a recombinant DNA molecule comprising a plasmid and the DNA fragment operationally inserted therein. Alternatively, the host microorganism may be transformed by integrating the DNA fragment of the present invention into the host chromosomal DNA.

Preferably, the DNA fragment is derived from an alfalfa plant, and most preferably, it is derived from a *Medicago sativa* strain. In another preferred embodiment, the plant-derived DNA fragment is modified by one or more nucleotide substitutions, deletions and/or insertions. Most preferably, the modification comprises deleting the nucleotides encoding the amino acid sequence: Met-Ala-Ser-Ile-Asp-Ala-Gln-Leu-Arg.

Further, as described above, it is acceptable that the DNA sequence of the present invention is inserted into vector DNA capable of self-replication and introduced into the host. As the vector DNA, a plasmid vector is preferable, and those capable of self-replication in a host cell are most preferable. Alternatively, a vector of phage DNA can be also utilized.

When the DNA fragment containing a gene is derived from a plant of the class Monocotyledonae or Dicotyledonae or from a microorganism belonging to the genus Corynebacterium or Brevibacterium, it is also acceptable that the DNA fragment is integrated into the chromosomal DNA of a host microorganism by means of a method using, for example, transposons (Berg, D. E. and Berg, C. M., *Bio/Technol.* 1:417 (1983)), Mu phage (Japanese Patent Laid-open No.2-109985) or homologous recombination (*Experiments in Molecular Genetics*, Cold Spring Harbor Lab. (1972)). In addition, in order to integrate the DNA of the present invention into the coryneform bacteria, it is possible to utilize a temperature-sensitive plasmid as disclosed in Japanese Patent Laid-open No. 5-7491.

In a preferred embodiment, the DNA fragment is derived from a *Corynebacterium glutamicum* strain and is integrated into the chromosomal DNA of a host microorganism. The region flanking the ppc gene in the *Corynebacterium glutamicum* chromosome has been sequenced (SEQ ID NO:3). According to the gene replacement strategy of the present invention, the chromosomal copy of the ppc gene is removed and replaced with an antibiotic resistance gene marker (FIG. 1). The marker is in turn replaced with a modified ppc gene of the present invention.

The unique design of this gene replacement strategy facilitates complete removal of the chromosomal ppc DNA sequence of a host microorganism and substitution of a new ppc gene without altering the expression of the two neighboring genes, the tpi gene and the secG gene. The tpi gene encodes the glycolytic enzyme triosephosphate isomerase, and the secG gene encodes secG, an integral membrane protein involved in protein export.

The design of this gene replacement strategy depends upon the reconstitution of intact tpi and secG genes that flank the ppc gene. Four oligonucleotides can be used to clone the DNA regions flanking ppc:

| | |
|---|---|
| 5' GTTGG TGAGC CACTG GAAAT CCGTG 3' (SEQ ID:NO 4) | (1) |
| 5' GATGT CATCG CGTAA AAAAT CAGTC 3' (SEQ ID:NO 5) | (2) |
| 5' CACTG CGCTG CGCAA CTCTA GATAG 3' (SEQ ID:NO 6) | (3) |
| 5' GACCA CCACC TTGCC GAAAT CTTGG 3' (SEQ ID:NO 7). | (4) |

In another aspect of the present invention there is provided a method of producing an amino acid by fermentation. The method comprises cultivating a host microorganism belonging to the genus Escherichia, Corynebacterium or Brevibacterium in a suitable medium and isolating from the culture medium an amino acid, wherein the host microorganism is transformed with a DNA fragment comprising a gene encoding a polypeptide having PEP carboxylase activity, wherein the host microorganism expresses the gene, and wherein the polypeptide does not require acetyl-CoA for activation and is desensitized to feedback inhibition by aspartic acid.

The method for cultivating the aforementioned hosts is not especially different from a cultivation method for amino acid-producing microorganisms in the prior art. Namely, an ordinary medium is used containing a carbon source, a nitrogen source, inorganic ions, substances satisfying nutrient auxotrophy, and optionally organic trace nutrients such as amino acids, vitamins and the like.

As the carbon source, carbohydrates such as glucose, sucrose, lactose, etc., as well as organic acids such as acetic acid may be used. As the nitrogen source, ammonia gas, aqueous ammonium, ammonium salt and the like can be used. As inorganic ions, potassium ions, sodium ions, magnesium ions, phosphate ions, and the like are appropriately added to the media as required.

The cultivation is performed until the generation and accumulation of the amino acid substantially stops while suitably controlling pH and temperature of the medium under an aerobic condition. In order to collect amino acids thus accumulated in the cultivated medium, an ordinary method can be applied. For example, after the removal of the cells by filtration, ultrafiltration, centrifugation or other known means, the amino acid is recovered, for example, by concentration of the cell-free solution and crystallization of the amino acid (or a salt thereof). Alternatively, the compound can be recovered by ion exchange chromatography.

In a preferred embodiment, the amino acid is one which is derived from OAA, such as L-aspartate, L-lysine, L-methionine, L-threonine and L-isoleucine. Most preferably, the amino acid is L-lysine.

In another aspect of the invention there is provided a method of increasing the rate of conversion of PEP to OAA. The method comprises transforming a host microorganism with a DNA fragment of the present invention. In a preferred embodiment, the host microorganism is selected from the genus Escherichia, Corynebacterium or Brevibacterium.

PEP carboxylase catalyzes the condensation reaction between PEP and carbon dioxide resulting in the formation of OAA. A PEP carboxylase of the present invention that is not substantially regulated by acetyl-CoA or aspartic acid therefore increases the rate of conversion of PEP to OAA.

In the case wherein the DNA fragment is derived from a plant belonging to the class Monocotyledonae or Dicotyledonae, transformation may be by integration or by utilization of a recombinant DNA molecule, for example. In the case wherein the DNA fragment is derived from a microorganism belonging to the genus Corynebacterium or Brevibacterium, the host microorganism is transformed by the integration of the DNA fragment of the invention into the chromosomal DNA of the host microorganism.

In another aspect of the invention there is provided a method of recycling carbon in a fermentation process. The method comprises transforming a host microorganism with a DNA fragment of the present invention. In a preferred embodiment, the host microorganism is selected from the genus Escherichia, Corynebacterium or Brevibacterium.

The TCA cycle requires continuous replenishment of $C_4$ molecules in order to replace the intermediates withdrawn for amino acid biosynthesis. PEP carboxylase aids in fulfilling this function by playing an anaplerotic role in supplying the four carbon OAA to the TCA cycle. By transforming a host microorganism with the DNA fragment of the present invention which codes for a polypeptide having PEP carboxylase activity, a method for recycling carbon is thereby provided.

In the case wherein the DNA fragment is derived from a plant belonging to the class Monocotyledonae or Dicotyledonae, transformation may be by integration or by utilization of a recombinant DNA molecule, for example. In the case wherein the DNA fragment is derived from a microorganism belonging to the genus Corynebacterium or Brevibacterium, the host microorganism is transformed by the integration of the DNA fragment of the invention into the chromosomal DNA of the host microorganism.

L-lysine and L-glutamic acid have been hitherto industrially produced by fermentative methods by using coryneform bacteria belonging to the genus Brevibacterium or Corynebacterium having abilities to produce these amino acids. In these methods, it is known that the coryneform bacteria require biotin for their growth. The enzyme PEP carboxylase does not require biotin for biological activity. In addition, one of the major physiological roles of PEP carboxylase is to replenish the TCA cycle by the assimilation of carbon. The de-regulated PEP carboxylase of the present invention improves the assimilation of carbon dioxide.

Therefore, in another aspect of the invention there is provided a method of assimilating carbon in a fermentation process which does not require biotin.

The method comprises transforming a host microorganism with a DNA fragment of the present invention. In a preferred embodiment, the host microorganism is selected from the genus Escherichia, Corynebacterium or Brevibacterium.

In the case wherein the DNA fragment is derived from a plant belonging to the class Monocotyledonae or Dicotyledonae, transformation may be by integration or by utilization of a recombinant DNA molecule, for example. In the case wherein the DNA fragment is derived from a microorganism belonging to the genus Corynebacterium or Brevibacterium, the host microorganism is transformed by the integration of the DNA fragment of the invention into the chromosomal DNA of the host microorganism.

The anaplerotic enzyme PEP carboxylase is critical to the maintenance of an optimal pool of OAA, and consequently determines the biosynthetic levels of organic acids deriving from it. By transforming a host microorganism with the DNA fragment of the present invention, the rate of production of OAA is increased. As such, the production of organic acids derived from OAA is increased as well.

Accordingly, in yet another aspect of the present invention there is provided a method of increasing the production of organic acids in a fermentation process. In a preferred embodiment, the host microorganism is selected from the genus Escherichia, Corynebacterium or Brevibacterium.

In the case wherein the DNA fragment is derived from a plant belonging to the class Monocotyledonae or Dicotyledonae, transformation may be by integration or by utilization of a recombinant DNA molecule, for example. In the case wherein the DNA fragment is derived from a microorganism belonging to the genus Corynebacterium or Brevibacterium, the host microorganism is transformed by the integration of the DNA fragment of the invention into the chromosomal DNA of the host microorganism.

OAA is an important substrate for the production of cell metabolites such as amino acids. By increasing the rate of conversion of PEP to OAA, the ppc genes of the invention thereby increase the production of amino acids. Therefore, in another aspect of the invention there is provided a method of increasing the production of amino acids in a fermentation process. The method comprises transforming a host microorganism with a DNA fragment of the present invention.

In a preferred embodiment, the host microorganism is selected from the genus Escherichia, Corynebacterium or Brevibacterium. In another preferred embodiment, the amino acid comprises L-aspartate, L-lysine, L-methionine, L-threonine and L-isoleucine. Most preferably, the amino acid is L-lysine.

In the case wherein the DNA fragment is derived from a plant belonging to the class Monocotyledonae or Dicotyledonae, transformation may be by integration or by utilization of a recombinant DNA molecule, for example. In the case wherein the DNA fragment is derived from a microorganism belonging to the genus Corynebacterium or Brevibacterium, the host microorganism is transformed by the integration of the DNA fragment of the invention into the chromosomal DNA of the host microorganism.

All patents and publications cited in this disclosure are indicative of the level of skill of those skilled in the art to which this invention pertains and are all herein incorporated by reference in their entirety.

Having now generally described the invention, the same will be more readily understood through reference to the following Examples which are provided by way of illustration, and are not intended to be limiting of the present invention, unless specified.

EXAMPLE 1

A Plant ppc Gene Functions in *Escherichia coli*

The cDNA clone (A PPC) of the ppc gene from alfalfa (*Medicago sativa*) was functional in the *Escherichia coli* mutant CGSC3594 which lacks a functional PEP carboxylase and cannot grow on M9 medium with glucose as the sole carbon source. When transformed with the A PPC plasmid (pMS2), *E. coli* mutant CGSC3594 was able to grow on M9 medium with glucose as the sole carbon source. The DNA and amino acid sequences of the alfalfa PEP carboxylase are provided in SEQ ID NO:1 and SEQ ID NO:2, respectively.

EXAMPLE 2

The ppc Gene from Alfalfa Shows Growth Stimulation in Corynebacterium in Shake Flasks The effect of the ppc gene from alfalfa (*Medicago sativa*) on growth stimulation in the lysine-producing Corynebacterium strain BF100 was determined. Growth was measured as the optical density at 660 nm, the titer was measured as g lysine/liter of medium, and the yield was measured as (g lysine/g glucose consumed)×100. 30 mg/L of isopropyl-beta-D-galactoside (IPTG), an inducer, was present. The results are shown in Table 1:

TABLE 1

| Strain | Growth | Titer | Yield |
| --- | --- | --- | --- |
| BF100 | 25 | 25 | 42 |
| BF100/pMS2 | 34 | 23 | 40 |
| BF100/pMS2/IPTG | 40 | 25 | 43 |

EXAMPLE 3

The ppc Gene from a Wild-Type Corynebacterium Strain Improves Productivity of a Lysine-Producing Corynebacterium Strain The cDNA clone (CPPC) of the ppc gene from *Corynebacterium glutamicum* ATCC 13032 was inserted into the pCPPC plasmid. When lysine producing *Corynebacterium glutamicum* strain BF100 was transformed with the pCPPC plasmid in shake flasks, the productivity was improved.

Growth was measured as the optical density at 660 nm, the titer was measured as g lysine/liter of medium, and the yield was measured as (g lysine/g glucose consumed)×100. The results are shown in Table 2:

TABLE 2

| Strain | Growth | Titer | Yield |
| --- | --- | --- | --- |
| BF100 | 39 | 27 | 44 |
| BF100/pCPPC | 32 | 29 | 48 |

EXAMPLE 4

Sensitivities to Acetyl-CoA and L-Aspartic Acid from Wild-type and Lysine-Producing Corynebacterium Strains Different sensitivities to acetyl-CoA and L-aspartic acid were observed in extracts from a wild-type *Corynebacterium glutamicum* strain (ATCC 13032) and a lysine-producing *Corynebacterium glutamicum* strain (BF100) as determined by PEP carboxylase activity. Activity units were measured spectrophotometrically as the change in absorbance (340 nm/min) using crude extracts. The results are shown in Table 3:

TABLE 3

| | PEP Carboxylase Activity | | |
| --- | --- | --- | --- |
| Strain | Complete | −Acetyl CoA | +Aspartate (5 mM) |
| ATCC 13032 | 100% | 56% | 100% |
| BF100 | 100% | 15% | 17% |

EXAMPLE 5

Replacement of a Chromosomal ppc Gene with a Modified ppc Gene

The region flanking the ppc gene in the *Corynebacterium glutamicum* chromosome has been sequenced (SEQ ID NO:3). The chromosomal copy of the ppc gene is removed and replaced with an antibiotic resistance gene marker (FIG. 1). The marker is in turn replaced with a modified ppc gene of the present invention. The unique design of this gene replacement strategy facilitates complete removal of the chromosomal ppc DNA sequence of a host microorganism and substitution of a new gene without altering the expression of the two neighboring genes.

The design of this gene replacement strategy depends upon the reconstitution of intact tpi and secG genes that flank the ppc gene. Four oligonucleotides can be used to clone the DNA regions flanking ppc:

5' GTTGG TGAGC CACTG GAAAT CCGTG 3'
(SEQ ID:NO 4) (1)

5' GATGT CATCG CGTAA AAAAT CAGTC 3'
(SEQ ID:NO 5) (2)

5' CACTG CGCTG CGCAA CTCTA GATAG 3'
(SEQ ID:NO 6) (3)

5' GACCA CCACC TTGCC GAAAT CTTGG 3'
(SEQ ID:NO 7). (4)

In view of the foregoing description taken with the Examples, those skilled in the art will be able to practice the invention in various enablements and embodiments without departing from the spirit and scope of the invention as defined in the appended claims.

What is claimed is:

1. An isolated DNA fragment comprising a gene encoding a polypeptide having the amino acid sequence of SEQ ID NO:2, wherein said gene is capable of being expressed in a host microorganism comprising the genus Escherichia, Corynebacterium and Brevibacterium, wherein the nucleotides of said gene encoding the amino acid sequence: Met-Ala-Ser-Ile-Asp-Ala-Gln-Leu-Arg are deleted and wherein said polypeptide does not require acetyl coenzyme A for activation and is desensitized to feedback inhibition by aspartic acid.

2. The DNA fragment of claim 1, wherein said DNA fragment is cDNA, genomic DNA or synthetic DNA.

3. An isolated DNA fragment derived from a microorganism belonging to the genus Corynebacterium comprising a gene encoding a polypeptide having phosphoenolpyruvate carboxylase activity, wherein said gene is set forth in SEQ ID NO: 3, and is capable of being expressed in a host microorganism comprising the genus Escherichia, Corynebacterium and Brevibacterium, wherein said gene is integrated into chromosomal DNA of said host microorganism, and wherein said polypeptide does not require acetyl coenzyme A for activation and is desensitized to feedback inhibition by aspartic acid.

4. The DNA fragment of claim 3, wherein said DNA fragment is derived from a *Corynebacterium glutamicum* strain.

5. The DNA fragment of claim 3, wherein said gene is integrated by removing the chromosomal ppc gene of the host microorganism and inserting said gene encoding a polypeptide having phosphoenolpyruvate carboxylase activity without altering the expression of the two genes flanking the chromosomal ppc gene of the host microorganism.

6. A recombinant DNA molecule comprising a plasmid and a gene encoding a polypeptide having the amino acid sequence of SEQ ID NO:2 operationally inserted therein, wherein said recombinant DNA molecule is capable of propagating and said gene is capable of being expressed in a host microorganism comprising the genus Escherichia, Corynebacterium and Brevibacterium, wherein the nucleotides of said gene encoding the amino acid sequence: Met-Ala-Ser-Ile-Asp-Ala-Gln-Leu-Arg are deleted, and wherein said polypeptide does not require acetyl coenzyme A for activation and is desensitized to feedback inhibition by aspartic acid.

7. A host microorganism belonging to the genus Escherichia, Corynebacterium or Brevibacterium transformed with an isolated DNA fragment comprising a gene encoding a polypeptide having the amino acid sequence of SEQ ID NO:2, wherein the nucleotides of said gene encoding the amino acid sequence: Met-Ala -Ser-Ile-Asp-Ala-Gln-Leu-Arg are deleted, wherein said polypeptide does not require acetyl coenzyme A for activation and is desensitized to feedback inhibition by aspartic acid, and wherein said host microorganism transformed with said DNA fragment expresses said gene.

8. The host microorganism of claim 7, wherein said host microorganism is transformed by integrating said DNA fragment into the chromosomal DNA of said host microorganism or is transformed with a recombinant DNA molecule comprising a plasmid and said DNA fragment operationally inserted therein.

9. A host microorganism belonging to the genus Escherichia, Corynebacterium or Brevibacterium in which an isolated DNA fragment comprising a gene encoding a polypeptide having phosphoenolpyruvate carboxylase activity is integrated into the chromosomal DNA of said host microorganism, wherein said gene is set forth in SEQ ID NO: 3, wherein said isolated DNA fragment is derived from a microorganism belonging to the genus Corynebacterium, wherein said polypeptide does not require acetyl coenzyme A for activation and is desensitized to feedback inhibition by aspartic acid, and wherein said host microorganism expresses said gene.

10. The host microorganism of claim 9, wherein said DNA fragment is derived from a *Corynebacterium glutamicum* strain.

11. The host microorganism of claim 9, wherein said gene is integrated by removing the chromosomal ppc gene of the host microorganism and inserting said gene encoding a polypeptide having phosphoenolpyruvate carboxylase activity without altering the expression of the two genes flanking the chromosomal ppc gene of the host microorganism.

12. The DNA fragment of claim 1, wherein said gene comprises the nucleotide sequence of SEQ ID NO: 1, and wherein the nucleotides encoding the amino acid sequence Met-Ala-Ser-Ile-Asp-Ala-Gln-Leu-Arg is deleted from SEQ ID NO: 1.

13. The recombinant DNA molecule of claim 6, wherein said gene comprises the nucleotide sequence of SEQ ID NO: 1, and wherein the nucleotides encoding the amino acid sequence Met-Ala-Ser-Ile-Asp-Ala-Gln-Leu-Arg are deleted from SEQ ID NO: 1.

14. A host organism of claim 7, wherein said gene comprises the nucleotide sequence of SEQ ID NO: 1, wherein the nucleotides encoding the amino acid sequence Met-Ala-Ser -Ile-Asp-Ala-Gln-Leu-Arg are deleted from SEQ ID NO: 1.

15. The DNA fragment of claim 3, wherein said DNA fragment is cDNA, genomic DNA or synthetic DNA.

16. The host microorganism of claim 7, wherein said DNA fragment is cDNA, genomic DNA or synthetic DNA.

17. The host microorganism of claim 9, wherein said DNA fragment is cDNA, genomic DNA or synthetic DNA.

* * * * *